United States Patent
Splett

(10) Patent No.: US 6,477,422 B1
(45) Date of Patent: Nov. 5, 2002

(54) METHOD AND APPARATUS FOR CAPTURE DETECTION

(75) Inventor: Vincent E. Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/532,574

(22) Filed: Mar. 22, 2000

(51) Int. Cl.[7] ................................................. A61N 1/37
(52) U.S. Cl. ....................................................... 607/28
(58) Field of Search ............................. 607/28, 27, 13

(56) References Cited

U.S. PATENT DOCUMENTS

| | | |
|---|---|---|
| 4,727,877 A | 3/1988 | Kallok |
| 5,103,819 A | 4/1992 | Baker et al. |
| 5,158,078 A | 10/1992 | Bennette et al. |
| 5,320,643 A | 6/1994 | Roline et al. |
| 5,374,282 A | 12/1994 | Nichols et al. |
| 5,549,642 A | 8/1996 | Min et al. |
| 5,620,466 A | 4/1997 | Haefner et al. |
| 5,662,688 A | 9/1997 | Haefner et al. |
| 5,683,431 A | 11/1997 | Wang |
| 5,722,994 A | 3/1998 | Noren et al. |
| 5,861,013 A | 1/1999 | Peck et al. |
| 5,871,512 A | 2/1999 | Hemming et al. |
| 5,873,898 A | * 2/1999 | Hemming et al. ............ 607/28 |
| 5,987,356 A | 11/1999 | DeGroot |

* cited by examiner

Primary Examiner—Kennedy Schaetzle
(74) Attorney, Agent, or Firm—Girma Wolde-Michael

(57) ABSTRACT

The present invention permits discrimination between evoked response signals and post-pace polarization signals sensed by an implantable medical device by noting the polarity of the positive or negative change in voltage in respect of time (or dv/dt) of the waveform incident on the lead electrodes during a short period of time immediately following a paced event. It has been discovered that the post-pace polarization signal exhibits a relatively constant polarity during the capture detect window, and that the evoked response signal may cause the polarity of post-pace polarization signal to reverse during the capture detect window. The sign of the post-pace polarization polarity, either positive or negative, is determined by the design of the specific output circuitry. The evoked response signal may, reverse the polarity of the sensed signal in either case, from positive to negative or from negative to positive, during the time window of interest. When the magnitude of the post-pace polarization is so great that the evoked response does not reverse the polarity of the waveform, discrimination of the evoked response can be achieved by comparing the sensed signal with a variable threshold for a defined duration. In another embodiment, if the amplitude of the sensed signal is not indicative of polarization, a constant sensing threshold for capture detection is employed.

22 Claims, 5 Drawing Sheets

METHOD AND APPARATUS FOR CAPTURE DETECTION

FIELD OF THE INVENTION

The present invention generally relates to implantable pacemakers, cardioverters and defibrillators and more particularly to a method and apparatus for testing and detecting capture of the heart in response to a pacing pulse energy, deriving and storing stimulation threshold data, and adjusting pacing pulse energy for energy efficiency.

BACKGROUND OF THE INVENTION

A cardiac pacemaker implantable pulse generator (IPG) is an electrical device used to supplant some or all of an abnormal heart's natural pacing function by delivering appropriately timed electrical stimulation signals designed to cause the myocardium of the heart to contract or "beat", i.e. to "capture" the heart. Stimulation pulses provided by implanted pacemakers usually have well-defined amplitude and pulse width characteristics which can be adjusted by remote programming and telemetry equipment to meet physiologic and device power conservation needs of the particular patient.

The strength (amplitude) and duration (pulse width) of the pacing pulses must be of such an energy magnitude above the stimulation threshold that capture is maintained to prevent serious complications and even death. Yet, it is desirable for these energy magnitudes not to be higher than the stimulation threshold than is needed for a reasonable "safety margin" in order to prolong battery life.

As a result of these considerations, a great deal of effort has been expended over many years to develop pacemaker IPGs having the capability of automatically testing the stimulation threshold, i.e. providing an "auto-capture" detection function, and resetting the pacing pulse energy to exceed the threshold by the safety margin without the need for clinical or patient intervention. A variety of approaches have been taken as reflected by the extensive listing of earlier patents described in commonly assigned U.S. Pat. No. 5,324,310 issued to Greeninger, et al., 5,320,643 issued to Roline, et al., 5,871,512, issued to Hemming, et al. and 5,861,013 issued to Peck et al., all incorporated herein by reference in their entireties.

In such pacemaker IPGs, capture detection approaches have taken a variety of forms in the attempt to overcome the difficulty in detecting the evoked cardiac response wave shape due to polarization of the pacing electrodes employed to deliver the pacing pulse. Some of the approaches that have been taken include blanking intervals for the sense amplifiers combined with efforts to suppress or attenuate or compensate electronically for the post-delivery electrode polarization signal.

The Peck, et al. and Hemming, et al. patents cited above disclose capture detection mechanisms in which a reference voltage in a capture detection circuit is continuously updated and decreased in value as the sense amplifier tracks the sensed signal provided that dV/dt of the sensed signal is less than zero or substantially less than zero. When or if dV/dt of the sensed signal becomes equal to zero or substantially equal to zero, that reference voltage is held to the minimum value, or "negative peak," it attained during the period of time when dV/dt of the sensed signal was less negative. When or if dV/dt becomes positive or substantially positive thereafter, the difference between the sensed signal and the minimum value attained and tracked previously is amplified. The term "negative peak tracking" is used to describe the operation of the foregoing circuit and method.

Alternatively, the use of separate "far field" EGM amplifiers and electrode systems from those "near field" electrode systems used in delivering the pacing pulse has been proposed in a variety of configurations, as exemplified by the above referenced '310 patent. The use of cardioversion/defibrillation electrodes for capture detection is disclosed in U.S. Pat. No. 5,683,431 issued to Wang, also incorporated herein by reference in its entirety.

SUMMARY OF THE INVENTION

The present invention is directed toward providing an improved capture detection mechanism, which can reliably distinguish between capture and non-capture, following a delivered pacing pulse. In the particular embodiment disclosed, cardioversion/defibrillation electrodes are employed for capture detection, as generally suggested in the above-cited Wang patent. In particular, a right ventricular cardioversion electrode and a subcutaneous cardioversion electrode, for example, taking the form of the housing of the associated implantable pacemaker/cardioverter/defibrillator may be employed. While the specific embodiment discussed herein is directed toward implementation of the invention in the context of an implantable pacemaker/cardioverter/defibrillator, as discussed below, the invention is also believed valuable in the context of devices in which other electrodes, including pacing electrodes, are employed to detect capture. The present invention is particularly desirable for use in devices which may employ an electrode set in which one of the electrodes employed to deliver a pacing pulse is also employed for capture detection.

When the invention is practiced in the context of a pacemaker/cardioverter/defibrillator as disclosed herein, it may be usefully employed in conjunction with cardioversion/defibrillation electrode systems employing either "true bipolar" pacing and sensing or "integrated bipolar" pacing and sensing. In the case of a device employing "true bipolar" sensing, the cardioversion/defibrillation lead system is provided with a pair of smaller surface area pacing electrodes, dedicated to delivering cardiac pacing pulses and sensing heart depolarizations. In the case of a cardioversion/defibrillation lead system employing an "integrated bipolar" electrode system, a small surface area pacing electrode in conjunction with a large surface area cardioversion/defibrillation electrode are employed for cardiac pacing and sensing.

In cardioversion/defibrillation lead systems employing true bipolar pacing and sensing, residual polarization of cardioversion/defibrillation electrodes following delivery of a pacing pulse is minimal. In such cases, the present invention is adapted to detect capture by simply determining that the sensed signal following the delivered pacing pulse exceeds a defined threshold, preferably for a defined period. In the case of a cardioversion/defibrillation electrode system employing integrated bipolar pacing and sensing, some post-pacing polarization may remain on the cardioversion/defibrillation electrode employed during pacing. The capture detection mechanism of the present invention is also adapted to accurately detect capture in such cases, by means of a self-adjusting sensing threshold.

Following delivery of a pacing pulse, the capture detection mechanism of a preferred embodiment of the present invention checks to determine whether significant polarization remains on one or both of the electrodes employed for capture detection. For example, in the case of a device employing a cardioversion/defibrillation lead system employing integrated bipolar sensing and pacing, the capture detection mechanism of the present invention would first check the signal amplitude between the electrodes employed for capture detection, e.g., the right ventricular and subcutaneous cardioversion/defibrillation electrodes. In this embodiment, if no significant polarization signal level is present shortly following the pacing pulse, the capture detection mechanism simply determines whether the signal amplitude following delivery of the pacing pulse exceeds a defined threshold for a defined time interval. If the a signal level following delivery of the pacing pulse indicates that polarization is present on one or both of the capture detection electrodes, the mechanism of the present invention employs an alternative mechanism for capture detection, optimized to detect capture in the presence of post-pacing pulse polarization.

As described in the above-cited Peck, et al and Hemming, et al. patents, negative peak tracking can be employed to determine whether a cardiac pacing pulse has been successful in capturing the heart, in most cases. However, it has been determined by the inventor that the required reversal of slope required to allow the negative peak detector to function is not necessarily always present, even in the context of a pacing pulse that successfully captures the heart. For this reason, in the presence of electrode polarization, the capture detection mechanism of the preferred embodiment of the present invention instead relies upon a detection threshold that decreases with time to a defined constant threshold level. The decreasing portion of the threshold preferably declines linearly and is defined as a function of the waveform of the composite electrode polarization/heart depolarization polarization signal following delivery of the pacing pulse. The detection mechanism of the present invention defines a line extending from the detected peak of the polarization waveform and the lowest point following the polarization waveform, within a defined maximum time interval, e.g., 30 milliseconds. The slope of this line is then reduced by a scaling factor, e.g., 1.5, to define a variable detection threshold. Signals which persist above the higher of this linearly decreasing detection threshold and the defined constant threshold level for a defined duration threshold, e.g., 10 milliseconds, are considered to be an indication of successful capture of the heart. In the disclosed embodiment, the constant threshold level is fixed, however, in other embodiments this threshold may be variable either by physician programming or by means of an automatic sensing threshold adjustment mechanism as known to the art, for example by means of a mechanism in which the value of the constant threshold is varied as a function of the amplitude of previous sensed depolarization waveforms.

By the mechanism of the present invention, capture can be detected even in the event that the composite polarization/heart depolarization wave form does not display the negative peak required by the capture detection mechanism of the Peck, et al. and Hemming, et al. patents. Testing of the capture detection mechanism of the present invention by the inventors indicates that it provides a highly reliable mechanism of distinguishing between capture and non-capture in conjunction with cardioversion/defibrillation lead systems employing "integrated bipolar" sensing, particularly those employing the right ventricular and subcutaneous cardioversion/defibrillation electrodes for capture detection.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The embodiment of the invention as described below is implemented in the context of an implantable pacemaker/cardioverter/defibrillator (PCD) having single or dual chamber pacing and/or cardioversion/defibrillation capabilities of the types described in detail in U.S. Pat. No. 5,549,642, issued to Min, et al., U.S. Pat. No. 5,987,356, issued to DeGroot, U.S. Pat. No. 5,722,994, issued to Noren, et al. or U.S. Pat. No. 5,622,406, issued to Haefner, et al., all incorporated herein by reference in their entireties. Such PCDs may be constructed or made programmable to provide atrial only, ventricular only, or both atrial and ventricular pacing modes. The pacing modes also preferably include either or both bradycardia compensating pacing modes or anti-tachycardia pacing therapies. In addition, the present invention may be employed with a wide variety of defibrillation electrode combinations.

Figure 1:
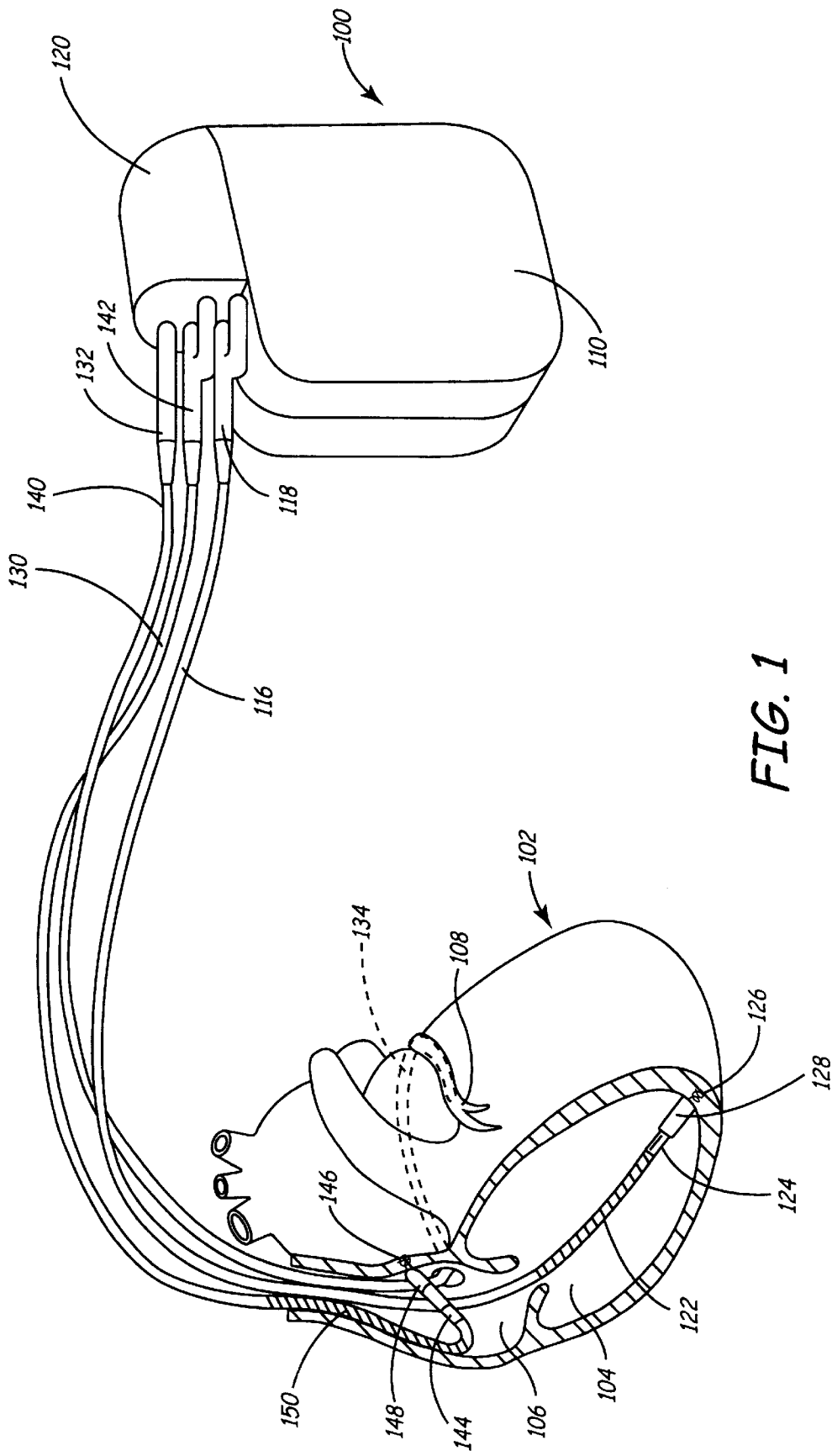
FIG. 1 is a schematic illustration of an atrial and ventricular chamber pacemaker/cardioverter/defibrillator IPG as implanted, with an IPG can electrode and endocardial leads transvenously introduced into the RA, CS and RV of the heart wherein capture of atrial and/or ventricular pacing pulses may be detected across selected threshold sensing electrode pairs.
Figure 2:
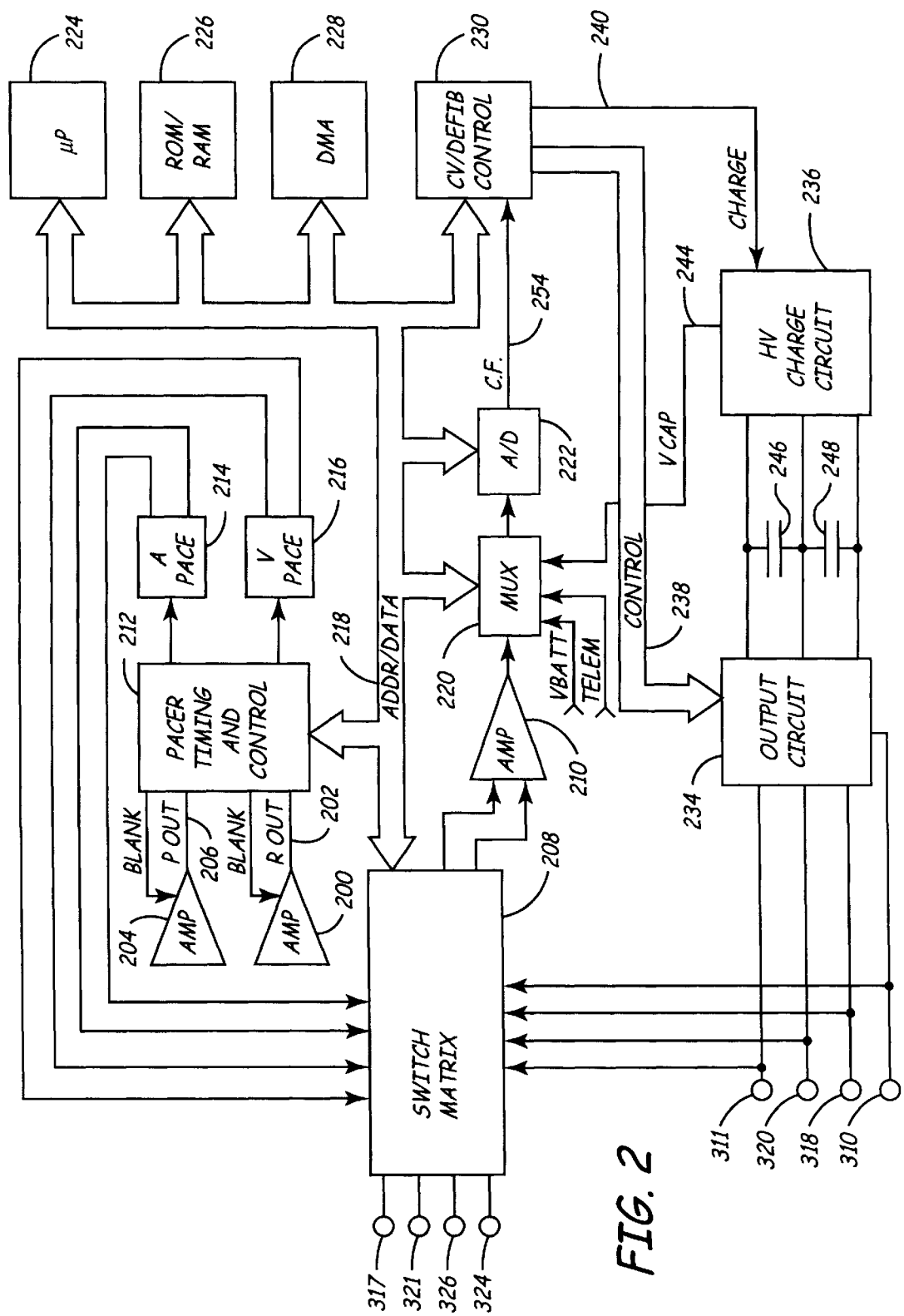
FIG. 2 is a block diagram of the IPG of FIG. 1 in which the present invention may be practiced by sensing the evoked response to a pacing pulse across a selected capture detection electrode pair.

FIGS. 1 and 2 illustrate a dual chamber, multi-programmable, PCD IPG and associated lead system for providing atrial and/or ventricular sensing functions for detecting P-waves of atrial depolarizations and/or R-waves of ventricular depolarizations, depending on the programmed pacing and/or sensing mode and delivering pacing or cardioversion/defibrillation therapies. An exemplary defibrillation lead system is depicted in FIG. 1 for delivering cardioversion/defibrillation shock therapies to the atria and/or ventricles of the heart. FIGS. 1 and 2 are intended to provide a comprehensive illustration of the various atrial and/or ventricular, pacing and/or cardioversion/defibrillation configurations that may be effected using sub-combinations of the components depicted therein and equivalents thereto.

In the preferred embodiment of FIGS. 1 and 2, depending on the programmed pacing mode, pacing pulses may be applied to the atrium and/or ventricle in response to the detection of the appropriate bradycardia condition by the PCD IPG 100. The pacing and sensing functions are effected through atrial and ventricular bipolar pace/sense electrode pairs at the ends of right atrial/superior vena cava (RA/SVC) and right ventricular (RV) leads 130 and 116, respectively, fixed in the right atrium 106 and right ventricle 104, respectively, that are electrically coupled to the circuitry of IPG 100 through a connector block 120. Delivery of cardioversion or defibrillation shocks to the atrial and/or ventricular chambers of the heart 102 may be effected through selected combinations of the illustrated exemplary RA and RV defibrillation electrodes 150, 122 on the RA/SVC and RV leads and an additional coronary sinus (CS) electrode on a CS lead 140 as well as an exposed surface electrode 110 of the outer housing or can of the IPG 100. The can electrode 110 optionally serves as a subcutaneous defibrillation electrode, used as one electrode optionally in combination with one intracardiac defibrillation electrode for cardioverting or defibrillating either the atria or ventricles. A remote, subcutaneous defibrillation patch electrode may be provided in addition to or substitution for the can electrode 110.

The RV lead 116 is depicted in a "true bipolar" configuration and includes an elongated insulating lead body, enclosing three electrically isolated conductors. Located adjacent the distal end of the RV lead 116 are a pace/sense ring electrode 124, a helical, pace/sense electrode 126, mounted retractably within an insulating electrode head 128. Helical electrode 126 is adapted to be extended out of the electrode head 128 and screwed into the ventricular apex in a manner well known in the art. RV pace/sense electrodes 124 and 126 are each coupled to conductors within the RV lead body and are employed for cardiac pacing in the ventricle and for sensing near-field R-waves. RV lead 116 also supports an elongated, exposed wire coil, defibrillation electrode 122 in a distal segment thereof adapted to be placed in the right ventricle 104 of heart 102. The RV defibrillation electrode 122 may be fabricated from platinum, platinum alloy or other materials known to be usable in implantable defibrillation electrodes and may be about 5 cm in length. Defibrillation electrode 122 is also coupled to one of the conductors within the lead body of RV lead 116. At the proximal end of the lead body is a bifurcated connector end 118 having three exposed electrical connectors, each coupled to one of the conductors and attached within the connector block 120 to connector block terminals in a manner well known in the art.

An "integrated bipolar" lead for use in the right ventricle would correspond to lead 116 as illustrated, with ring electrode 124 and its associated conductor and connector deleted. In such case, ventricular defibrillation electrode 122 would be used for ventricular pacing and sensing in conjunction with pace/sense electrode 126.

The coronary sinus (CS) lead 130 includes an elongated insulating lead body enclosing one elongated conductor coupled to an elongated exposed coil wire defibrillation electrode 134. CS defibrillation electrode 134, illustrated in broken outline, is located within the coronary sinus and great vein 108 of the heart 102 and may be about 5 cm in length. At the proximal end of the CS lead 140 is a connector end 132 having an exposed connector coupled to the conductor and attached within the connector block 120 to connector block terminals in a manner well known in the art.

The RA/SVC lead 130 is depicted in a "true bipolar" configuration and includes an elongated insulating lead body carrying three electrically isolated conductors, corresponding generally to the structure of the RV lead 116. The lead body is formed in a manner well known in the art in an atrial J-shape in order to position its distal end in the right atrial appendage. A pace/sense ring electrode 144 and an extendable helical, pace/sense electrode 146, mounted retractably within an insulating electrode head 148, are formed distally to the bend of the J-shape. Helical electrode 146 is adapted to be extended out of the electrode head 148 and screwed into the atrial appendage in a manner well known in the art. RA pace/sense electrodes 144 and 146 are employed for atrial pacing and for near-field sensing of P-waves. An elongated, exposed coil defibrillation RA/SVC electrode 150 is supported on RA lead 130 extending proximally to pace/sense ring electrode 144 and coupled to the third conductor within the RA lead body. Electrode 150 preferably is 10 cm in length or greater and is configured to extend from within the SVC and toward the tricuspid valve. At the proximal end of the RA lead 130 is a bifurcated connector 142 that carries three exposed electrical connectors, each coupled to one of the conductors and attached within the connector block 120 to connector block terminals in a manner well known in the art.

An "integrated bipolar" lead for use in the right atrium would correspond to lead 130 as illustrated, with ring electrode 144 and its associated conductor and connector deleted. In such case, atrial defibrillation electrode 150 would be used for atrial pacing and sensing in conjunction with pace/sense electrode 146.

In accordance with the present invention, the circuitry of FIG. 2 within PCD IPG 100 communicates with an external programmer (not shown) through an RF communication link in a manner well known in the art. The pacing pulse energy threshold for capturing the ventricle of heart 102 with pacing pulses delivered across the ventricular pace/sense electrodes 124 and 126 or 122 and 126 may be tested in a threshold determination operation initiated by commands from the external programmer. In addition, in accordance with the present invention, the circuitry itself may be programmed to initiate a capture detection sequence automatically on a periodic basis, e.g. when the patient is expected to be sleeping, to test for the capture/loss of capture stimulation threshold and to reset the stimulation pulse energy to a safety margin above the pacing pulse stimulation threshold generally as disclosed in U.S. Pat. No. 5,683,431 issued to Wang and incorporated herein by reference in its entirety. Alternatively, the capture detection mechanism may remain activated continuously and adjust pacing amplitude on a beat-by-beat basis, generally as disclosed in U.S. Pat. No. 5,320,643, issued to Thompson, et al, and incorporated herein by reference in its entirety. In either case, it is necessary to detect the evoked response, i.e., the heart depolarization waveform during the time that polarization after-potentials may be present as a result of the preceding pacing pulse. In the embodiment illustrated, ventricular capture detection is performed by sensing between cardioversion/defibrillation electrode 122 and the housing of the defibrillator or other subcutaneous electrode. Analogous determinations of capture detection in the atria may also be made employing electrode 150 and the housing of the defibrillator or other subcutaneous electrode.

FIG. 2 is a functional schematic diagram of the circuitry of a dual chamber, implantable pacemaker/cardioverter/defibrillator 100 in which the present invention may usefully be practiced. FIG. 2 should be taken as merely exemplary of the circuitry of a PCD IPG 100 in which the invention may be embodied, and not as limiting, as it is believed that the invention may usefully be practiced in a wide variety of device implementations.

The PCD IPG circuitry of FIG. 2 includes a high voltage section for providing relatively high voltage cardioversion/defibrillation shocks when needed in response to detection of a tachyarrhythmia, a low voltage pace/sense section for sensing P-waves and/or R-waves and providing relatively low voltage bradycardia pacing and anti-tachycardia pacing therapies, both operated under the control of a microcomputer including a microprocessor 224, ROM/RAM 226 and DMA 228. Other functions, including uplink and downlink telemetry with an external programmer for interrogating or programming operating modes and parameters, are also provided in a manner well known in the art.

The block diagram of FIG. 2 depicts the atrial and ventricular pace/sense and defibrillation lead connector terminals of the connector block 120. Assuming the electrode configuration of FIG. 1, the correspondence to the illustrated leads and electrodes is as follows: Terminal 310 is hard wired to electrode 110, that is, the un-insulated portion of the housing of the PCD IPG 100. Terminal 320 is adapted to be coupled through RV lead 116 to RV cardioversion/ defibrillation electrode 122. Terminal 311 is adapted to be coupled through RA lead 140 to RA/SVC electrode 150. Terminal 318 is adapted to be coupled through CS lead 130 to CS defibrillation electrode 134. However, it will be understood that fewer terminals may be provided than depicted, and/or that one or more differing defibrillation leads, e.g. epicardial patch electrode and subcutaneous patch electrode bearing leads may also be employed for one or more of the depicted defibrillation electrode bearing leads.

Terminals 310, 311, 318 and 320 are coupled to high voltage output circuit 234. High voltage output circuit 234 includes high voltage switches controlled by CV/DEFIB CONTROL logic 230 via control bus 238. The switches within circuit 234 control which electrodes are employed and which are coupled to the positive and negative terminals of the capacitor bank including capacitors 246 and 248 during delivery of the intermediate and high voltage cardioversion and defibrillation shocks.

Terminals 324 and 326 of the connector block are coupled through RV lead 116 to RV pace/sense electrodes 124 (if present) and 126 for sensing and pacing in the ventricle. Terminals 317 and 321 are coupled through RA/SVC lead 140 to RA pace/sense electrodes 144 (if present) and 146 for sensing and pacing in the atrium. A selected pair of terminals 320, 324 and 326 is coupled to the inputs of R-wave sense amplifier 200 through switches in switch network 208 to provide "true bipolar" or "integrated bipolar" sensing as described above. R-wave sense amplifier 200 preferably takes the form of an automatic gain controlled amplifier providing an adjustable sensing threshold as a function of the measured R-wave signal amplitude. A VSENSE signal is generated on R-OUT line 202 whenever the signal sensed between electrodes 124 and 126 or electrodes 12 and 126 exceeds the current ventricular sensing threshold. A selected pair of terminals 311, 317 and 321 is correspondingly coupled to the P-wave sense amplifier 204 through switches in switch network 208 to provide "true bipolar" or "integrated bipolar" sensing as described above. P-wave sense amplifier 204 preferably also takes the form of an automatic gain controlled amplifier providing an adjustable sensing threshold as a function of the measured P-wave amplitude. An ASENSE signal is generated on P-OUT line 206 whenever the signal sensed between electrodes 144 and 146 or electrodes 144 and 146 exceeds the current atrial sensing threshold.

The A-PACE and V-PACE output circuits 214 and 216 are also coupled to selected pairs of terminals 317, 321 and 311 or 324, 326 and 320, respectively by switch matrix 208, to provide "true bipolar" or "integrated bipolar" pacing as described above. The atrial and ventricular sense amplifiers 204 and 200 are isolated from the A-PACE and V-PACE output circuits 214 and 216 by appropriate isolation switches within switch matrix 208 and also by blanking circuitry operated by A-BLANK and V-BLANK signals during and for a short time following delivery of a pacing pulse in a manner well known in the art. The general operation of the R-wave and P-wave sense amplifiers 200 and 204 may correspond to that disclosed in U.S. Pat. No. 5,117,824, incorporated herein by reference in its entirety.

Switch matrix 208 is also used in an EGM sensing mode to select which of the available pace/sense electrodes (or defibrillation electrodes) are coupled to the inputs of EGM sense amplifier 210 for use in digital signal storage and analysis of the patient's atrial and ventricular EGM and for use in capture detection according to the present invention. Switches within switch matrix 208 are selectively controlled by the microprocessor 224 or circuits within the pacer timing and control circuitry 212, via data/address bus 218, to couple selected terminals, e.g. 321 and 311 or 326 and 320, to the inputs of bandpass amplifier 210 and to thereby apply atrial or ventricular signals to the bandpass amplifier 210. Output signals from bandpass amplifier 210, in response to the applied atrial or ventricular signals, are provided to multiplexer 220, and thereafter converted to multi-bit digital signals by A/D converter 222, for storage in RAM in ROM/RAM 226 under control of DMA 228. In conjunction with the present invention, microprocessor 224 may analyze the digitized signals following delivered pacing pulses in real time to implement the capture detection mechanism of the present invention and/or may analyze the stored digitized signals following delivery of a pacing pulse Microprocessor 224 may also employ digital signal and morphology analysis techniques to characterize the digitized signals stored in ROM/RAM 226 to recognize and classify the patient's heart rhythm employing any of the numerous signal processing methodologies known to the art.

The PCD IPG circuitry of FIG. 2 provides atrial and/or ventricular cardiac pacing for bradycardia and tachycardia conditions and synchronized cardioversion and defibrillation shock therapies for tachyarrhythmias in accordance with therapy regimes programmed by the physician. With respect to the pacing operations, the pacer timing and control circuitry 212 includes programmable digital counters which control the basic time intervals associated with bradycardia pacing modes including DDD, VVI, DVI, VDD, AAI, DDI and other modes of single and dual chamber pacing well known to the art. Pacer timing and control circuitry 212 also controls escape intervals associated with timing and delivering anti-tachyarrhythmia pacing in both the atrium and the ventricle, employing any anti-tachyarrhythmia pacing therapies known to the art. In the process, pacer timing and control circuitry 212 also times the operation of and processes ASENSE and VSENSE events on the P-OUT and R-OUT lines of the atrial and ventricular sense amplifiers 204 and 200. In the context of the present invention, pacer timing and control circuitry 212 responds to commands from microprocessor 224 to initiate a threshold determination operation and controls the switch matrix 208 to select the appropriate threshold sensing electrode pair, controls the use and operation of EGM amplifier 210 in the threshold detection operation, and processes the sensed events all as described below.

In normal pacing modes of operation, intervals defined by pacer timing and control circuitry 212 include atrial and ventricular pacing escape intervals, blanking intervals, the refractory periods during which sensed P-waves and R-waves are ineffective to restart timing of the escape intervals, and the pulse widths of the pacing pulses. These intervals are determined by microprocessor 224, in response to stored data in RAM in ROM/RAM 226 and are communicated to the pacer timing and control circuitry 212 via address/data bus 218. Pacer timing and control circuitry 212 also determines the amplitude of the cardiac pacing pulses under control of microprocessor 224.

During pacing, the escape interval counters within pacer timing and control circuitry 212 are reset upon sensing of R-waves and P-waves as indicated by a signals on lines 202 and 206. In accordance with the selected pacing mode, pacer timing and control circuitry 212 provides pace trigger signals to the A-PACE and V-PACE output circuits 214 and 216 on timeout of the appropriate escape interval counters to trigger generation of atrial and/or ventricular pacing pulses. The pacing escape interval counters are also reset on generation of pacing pulses, and thereby control the basic timing of cardiac pacing functions. The values of the counts present in the escape interval counters when reset by sensed R-waves and P-waves may be used as measures of the durations of R-R intervals, P-P intervals, P-R intervals and R-P intervals, which measurements are stored in RAM in ROM/RAM 226 and used to detect the presence of tachyarrhythmias as described below.

Microprocessor 224 operates as an interrupt driven device, and is responsive to interrupts from pacer timing and control circuitry 212 corresponding to the occurrence sensed P-waves (ASENSE) and R-waves (VSENSE) and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of RAM in the ROM/RAM 226 (FIG. 2) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. In the event that an atrial or ventricular tachyarrhythmia is detected, and an anti-tachyarrhythmia pacing regimen is prescribed, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation shock is required, microprocessor 224 employs an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246 and 248 via charging circuit 236, under control of high voltage charging control line 240. The voltage on the high voltage capacitors is monitored via VCAP line 244, and the monitored voltage signal is passed through multiplexer 220, digitized, and compared to a predetermined value set by microprocessor 224 in ADC/comparator 222. When the voltage comparison is satisfied, a logic signal on Cap Full (CF) line 254 is applied to cardioversion/defibrillation control circuit 230, terminating charging. Thereafter, timing of the delivery of the defibrillation or cardioversion shock is controlled by pacer timing/control circuitry 212. Following delivery of the fibrillation or tachycardia therapy, the microprocessor 224 then returns the operating mode to cardiac pacing and awaits the next successive interrupt due to pacing or the occurrence of a sensed atrial or ventricular depolarization.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, the polarity of the electrodes and which electrodes are involved in delivery of the pulse. An example of output circuitry for delivery of biphasic pulse regimens to multiple electrode systems may be found in U.S. Pat. No. 4,727,877, incorporated by reference in its entirety.

In the event that, as in FIGS. 1 and 2, both atrial and ventricular defibrillation are available, ventricular defibrillation may be accomplished using higher pulse energy levels than required for atrial defibrillation and may employ the same or a different electrode set. For example, terminals 310, 311, 318 and 320 or only terminals 311, 318 and 320 may be employed for atrial defibrillation. Terminals 311, 320 and 310 might be employed for ventricular defibrillation, with terminal 311 (coupled to RA/SVC electrode 150) coupled to terminal 310 (can electrode 110). Alternatively, terminals 310, 318 and 320 may be employed, with terminal 318 (coupled to CS electrode 134) coupled to terminal 310. As a further alternative, terminals 311, 310, 318 and 320 might all be employed for ventricular defibrillation, with terminals 310, 311 and 320 coupled in common. As yet another alternative, only terminals 310 and 320 might be employed for ventricular defibrillation, added or substituted for either of terminals 311 or 318 for treating ventricular fibrillation.

In the event that atrial or ventricular fibrillation is identified, the typical therapy will be delivery of a high amplitude defibrillation pulse, typically in excess of 10 joules in the case of ventricular fibrillation and about 1 joule or less in the case of atrial defibrillation. Lower energy levels will be employed for cardioversion. As in the case of currently available implantable pacemakers/ cardioverter/ defibrillators, and as discussed in the above-cited references, it is envisioned that the amplitude of the defibrillation pulse may be incremented in response to failure of an initial pulse or pulses to terminate fibrillation.

The detection criteria for detection of a tachyarrhythmia and the particular selection of the defibrillation terminals and associated defibrillation electrodes for delivery of the physician prescribed therapies are not of primary importance in the practice of the present invention. The method of the present invention, however, is only practiced when the HV charge circuit 236 is not being operated in response to a detected tachyarrhythmia and when cardioversion/defibrillation therapies are not being delivered.

Figure 3:
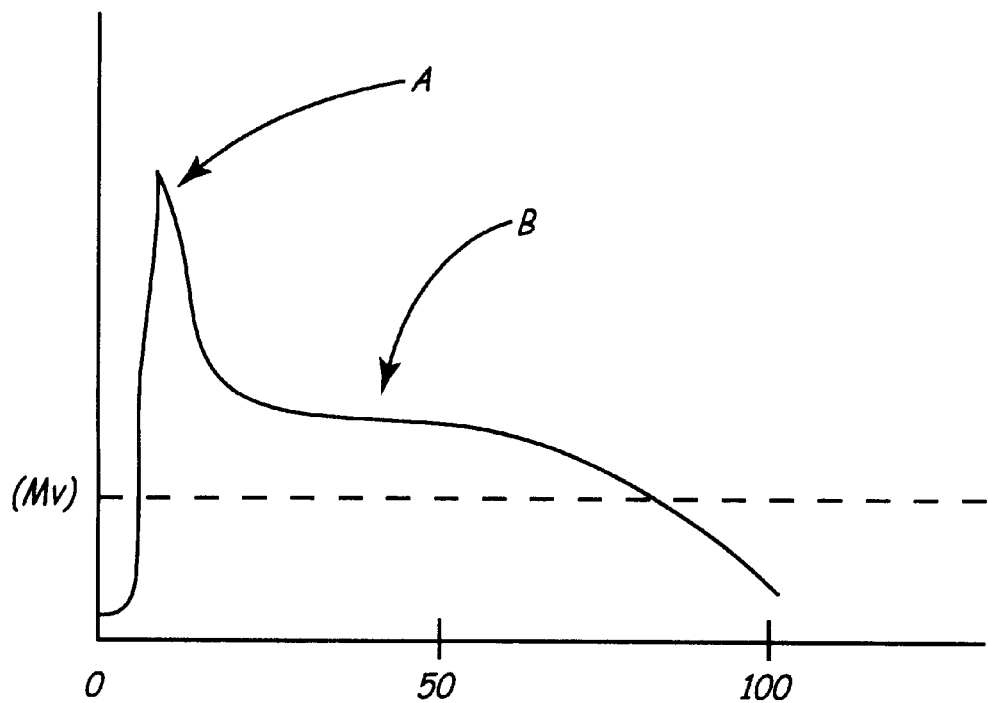
FIG. 3 illustrates a composite electrode polarization/ventricular depolarization waveform following a delivered pacing pulse.

FIG. 3 illustrates a composite electrode polarization/cardiac depolarization waveform following the pacing pulse, which does not display a negative peak as required by the capture detection mechanism of the above cited Peck and Hemming et al patents. The polarization signal reaches a peak at A, decreases rapidly thereafter to region B, the portion of the composite waveform indicative of the successful capture of the heart but not producing the negative peak required for capture detection by the Peck, et al. and Hemming, et al. patents.

Figure 4:
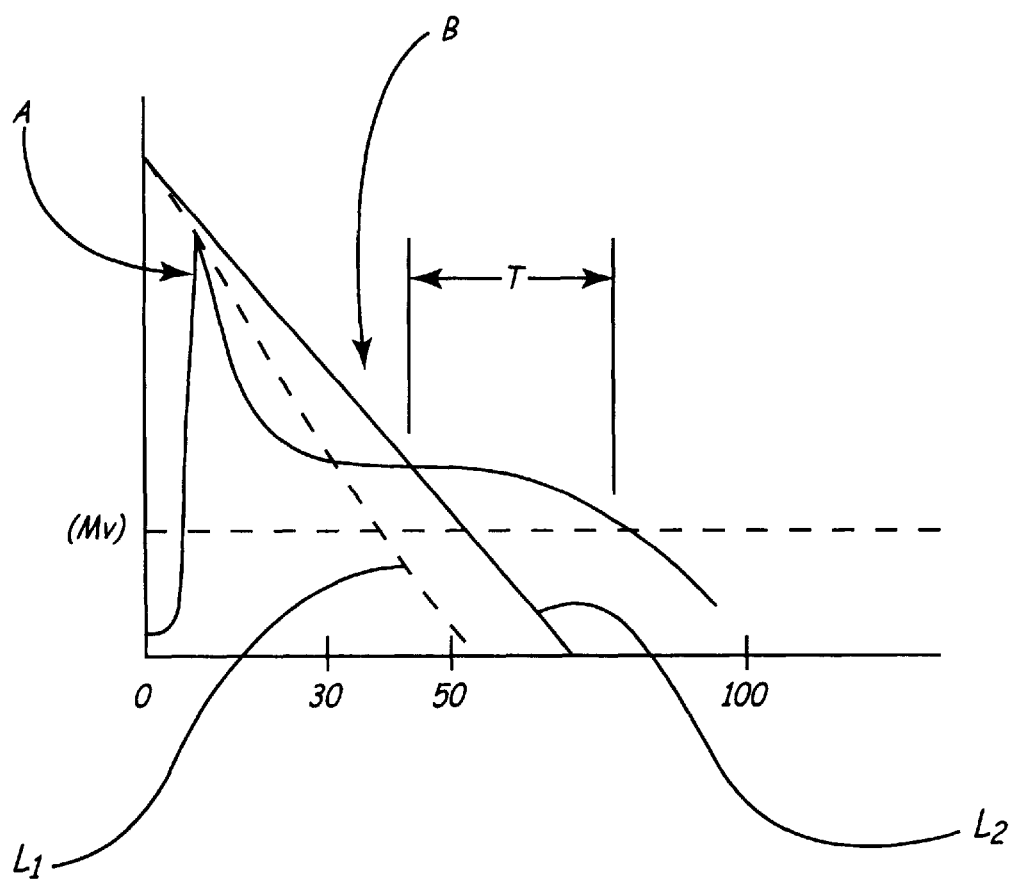
FIG. 4 illustrates the operation of the capture detection mechanism of the present invention, as applied to the waveform of FIG. 3.

FIG. 4 illustrates the operation of the capture detection mechanism of the present invention, as applied to the waveform of FIG. 3. After determining that polarization is present following the delivered pacing pulse, the capture detection mechanism of the present invention defines a line L1, connecting the polarization peak of the waveform to the lowest sensed amplitude of the waveform, occurring within a defined time limit, in this case 30 milliseconds. In the event that the negative peak manifests itself during this time period, of course, the negative peak will be employed in conjunction with the initial positive peak to define line L1. The calculation of line L1 is performed by the microprocessor 224 which correspondingly also calculates line L2, defined as a line passing through the Y axis at the same intersect as line L1, but having a slope reduced by scaling factor, e.g. 1.5. Line L2 in conjunction and a constant amplitude threshold, in this case illustrated as 1 millivolt, together define the effective sensing threshold employed by the capture detection mechanism of the present invention. The microprocessor 224 simply determines the duration of the time "T" during which the composite signal is above the higher of the linearly decreasing threshold defined by line L2 and the constant threshold, illustrated as 1 millivolt. If the duration of time T exceeds a defined minimum period, e.g. 10 milliseconds, the microprocessor 224 determines that the pacing pulse was successful in capturing the heart.

While the constant threshold as illustrated is fixed at one milli-volt, the value of the constant threshold may be adjusted either by programming or by means of an automatic threshold/automatic gain adjustment mechanism as in prior art defibrillators, in which the effective threshold varies as a function of the amplitude of previously sensed depolarizations. Exemplary systems which might be adapted for adjusting the constant threshold value are disclosed in U.S. Pat. No. 5,662,688, issued to Haefner, et al., U.S. Pat. No. 5,103,819, issued to Baker, et al., U.S. Pat. No. 5,374,282, issued to Nichols, et al, or U.S. Pat. No. 5,158,078, issued to Bennett, et al, all incorporated herein by reference in their entireties.

Figure 5:
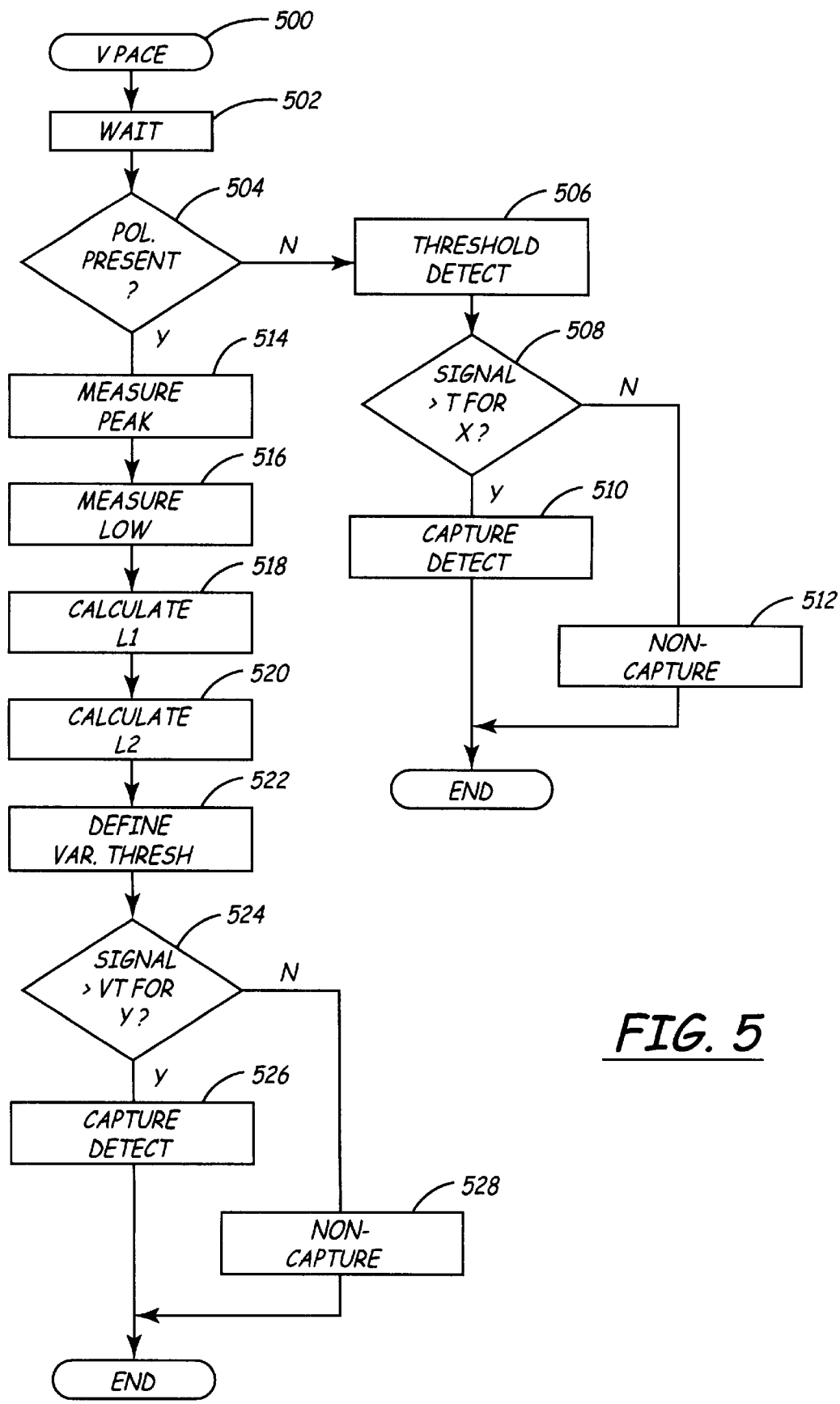
FIG. 5 is a functional flow chart, describing the overall operation of the capture detection mechanism of the present invention.

FIG. 5 is a flow chart illustrating the overall operation of the capture detection mechanism of the present invention, as applied to detection of ventricular capture. Following delivery of a cardiac pacing pulse at 500, the sense amplifier is blanked at 502 for a period of time sufficient to allow completion of the fast recharge pulse following delivery of the pacing pulse. This time interval may be, for example, on the range of 5 to 10 milliseconds. Thereafter, the signal sensed between the capture detection electrodes is evaluated at 504 by microprocessor 224 for a short period (e.g. 5–10 ms), to determine whether polarization is present. If not, at 506 the microprocessor 224 selects the first capture detection mechanism, employing a fixed detection threshold and it determines at 508 whether, during a defined capture detection interval, e.g. 100–150 milliseconds, following the delivered pacing pulse the sensed signal exceeds the defined threshold (e.g. 1 mV) for a preset time interval, e.g. 10 milliseconds. As discussed above, this would be the case if the ventricular defibrillation electrode 122 and the device housing 110 are used for capture detection (coupled to amplifier 210, FIG. 2), and "true bipolar" pacing and sensing is employed in the ventricle. If, during the capture detection interval, the digitized sensed signal exceeds the defined threshold for the preset time interval, the microprocessor 224 determines at 510 that capture has been detected. If not, the microprocessor determines at 512 that the pacing pulse has not captured the heart. The device then awaits the next activation of the capture detection feature in conjunction with the delivery of a subsequent pacing pulse.

In the event that polarization is detected following delivery of the pacing pulse, the microprocessor 224 determines the peak of the polarization portion of the signal at 514 and determines at 516 the minimum value of the signal within a defined duration following delivery of the pacing pulse, e.g., 30 milliseconds. The microprocessor 224 at 520 then calculates line L1 at 518, and, having calculated line L1, defines line L2 as described above, having the same Y intercept as L1, but a reduced slope. The calculated line L2, in conjunction with the constant threshold are employed to define a variable threshold at 522, as discussed above, and the microprocessor determines at 524 whether, during the capture detection interval as described above, the digitized waveform exceeds this defined variable threshold for a defined time period, e.g. 10 milliseconds. If so, the microprocessor determines at 526 that the pacing pulse has been successful in capturing the heart. If not, the microprocessor determines at 528 that the pacing pulse was not successful in capturing the heart. In the event that the constant threshold value is self-adjusting, as discussed above, the microprocessor performs any necessary calculations associated therewith, following detection of capture and/or following sensed spontaneous depolarizations of the heart.

The illustrated PCD IPG of FIG. 1 and block diagram of FIG. 2 are merely exemplary, and correspond to the general functional organization of most multi-programmable, microprocessor controlled, PCD devices presently commercially available. It is believed that the present invention is most readily practiced in the context of such an IPG architecture, and that the present invention can therefore readily be practiced using the basic hardware of existing microprocessor controlled, single chamber PCD IPGs, or in proposed dual chamber PCD devices of the types listed above. The invention may be implemented primarily by means of variations in the software stored in the ROM/RAM 226, switch matrix 208 and pacer timing and control circuitry 212 for the particular combinations of atrial and/or ventricular sense/pace and cardioversion/defibrillation functions in the particular PCD device configuration.

However, the present invention may also be usefully practiced in all such configurations by means of a full custom integrated circuit in each case. For example, such a circuit may take the form of a state machine in which a state counter serves to control an arithmetic logic unit to perform calculations according to a prescribed sequence of counter controlled steps.

While there has been shown what are considered to be the preferred embodiments of the invention, it will be manifest that many changes and modifications may be made therein without departing from the essential spirit of the invention.

It is intended, therefore, in the following claims to cover all such changes and modifications as may fall within the true scope of the invention.

In conjunction with the above disclosure, I claim:

1. A method of capture detection, comprising:

delivering a pacing pulse using an electrode;

following delivery of a pacing pulse, sensing an electrical signal using the electrode and monitoring the amplitude of the sensed electrical signal over time;

determining a polarization related amplitude of the sensed electrical signal;

employing the determined polarization related amplitude to define a variable sensing threshold which decreases with time; and detecting capture by the delivered pacing pulse responsive to the amplitude of the sensed electrical signal exceeding the variable sensing threshold for a defined duration.

2. The method of claim 1 wherein employing the determined polarization related amplitude to define a variable sensing threshold which decreases with time comprises defining a variable sensing threshold which decreases to a constant sensing threshold, which persists for a time period thereafter.

3. The method of claim 1 or claim 2 further comprising determining a second amplitude of the sensed electrical signal after the determined polarization related amplitude and wherein employing the determined polarization related amplitude to define a variable sensing threshold comprises employing the determined polarization related amplitude in conjunction with the determined second amplitude to define the variable sensing threshold.

4. The method of claim 3 wherein employing the determined polarization related amplitude to define a variable sensing threshold comprises defining a linearly decreasing sensing threshold.

5. The method of claim 1 wherein employing the determined polarization related amplitude to define a variable sensing threshold comprises defining a linearly decreasing sensing threshold.

6. A method of capture detection, comprising:

delivering a pacing pulse;

following delivery of a pacing pulse, sensing an electrical signal using an electrode and monitoring the amplitude of the sensed electrical signal over time;

determining whether the amplitude of the sensed electrical signal is indicative of electrode polarization;

if the amplitude of the sensed electrical signal is indicative of electrode polarization, employing a variable sensing threshold for capture detection; and if the amplitude of the sensed electrical signal is not indicative of electrode polarization, employing a constant sensing threshold for capture detection.

7. The method of claim 6, wherein employing a variable sensing threshold for capture detection comprises:

determining a polarization related amplitude of the sensed electrical signal;

employing the determined polarization related amplitude to define a variable sensing threshold which decreases with time; and detecting capture by the delivered pacing pulse responsive to the amplitude of the sensed electrical signal exceeding the variable sensing threshold for a defined duration.

8. The method of claim 7 wherein employing the determined polarization related amplitude to define a variable sensing threshold which decreases with time comprises defining a variable sensing threshold which decreases to a constant sensing threshold, which persists for a time period thereafter.

9. The method of claim 7 or claim 8 further comprising determining a second amplitude of the sensed electrical signal after the determined polarization related amplitude and wherein employing the determined polarization related amplitude to define a variable sensing threshold comprises employing the determined polarization related amplitude in conjunction with the second determined amplitude to define the variable sensing threshold.

10. The method of claim 9 wherein employing the determined polarization related amplitude to define a variable sensing threshold comprises defining a linearly decreasing sensing threshold.

11. The method of claim 6 wherein employing the determined polarization related amplitude to define a variable sensing threshold comprises defining a linearly decreasing sensing threshold.

12. A cardiac pacemaker, comprising:

means for delivering a pacing pulse using an electrode;

means for sensing an electrical signal using the electrode following delivery of a pacing pulse;

means for monitoring the amplitude of the sensed electrical signal over time;

means for determining a polarization related amplitude of the sensed electrical signal;

means for employing the determined polarization related amplitude to define a variable sensing threshold which decreases with time; and means for detecting capture by the delivered pacing pulse responsive to the amplitude of the sensed electrical signal exceeding the variable sensing threshold for a defined duration.

13. The apparatus of claim 1 wherein the means for employing the determined polarization related amplitude to define a variable sensing threshold comprises means for defining a variable sensing threshold which decreases to a constant sensing threshold, which persists for a time period thereafter.

14. The apparatus of claim 12 or claim 13 further comprising means for determining a second amplitude of the sensed electrical signal after the determined polarization related amplitude and wherein the means for defining a variable sensing threshold comprises means for employing the determined polarization related amplitude in conjunction with the second determined amplitude to define the variable sensing threshold.

15. The apparatus of claim 14 wherein the means for defining a variable sensing threshold comprises means for defining a linearly decreasing sensing threshold.

16. The apparatus of claim 12 wherein the means for defining a variable sensing threshold comprises means for defining a linearly decreasing sensing threshold.

17. A cardiac pacemaker, comprising:

means for delivering a pacing pulse;

means for sensing an electrical signal following delivery of a pacing pulse using an electrode;

means for monitoring the amplitude of the sensed electrical signal over time;

means for determining whether the amplitude of the sensed electrical signal is indicative of electrode polarization;

means responsive to a determination that the amplitude of the sensed electrical signal is indicative of electrode polarization, for employing a variable sensing threshold for capture detection; and means responsive to a determination that the amplitude of the sensed electrical signal is not indicative of electrode polarization, for employing a constant sensing threshold for capture detection.

18. The apparatus of claim 17, wherein the means for employing a variable sensing threshold for capture detection comprises:

means for determining a polarization related amplitude of the sensed electrical signal;

means for employing the determined polarization related amplitude to define a variable sensing threshold which decreases with time; and means for detecting capture by the delivered pacing pulse responsive to the amplitude of the sensed electrical signal exceeding the variable sensing threshold for a defined duration.

19. The apparatus of claim 18 wherein the means for defining a variable sensing threshold comprises means for defining a variable sensing threshold which decreases to a constant sensing threshold, which persists for a time period thereafter.

20. The apparatus of claim 18 or claim 19 further comprising means for determining a second amplitude of the sensed electrical signal after the determined polarization related amplitude and wherein the mean for defining a variable sensing threshold comprises means for employing the determined polarization related amplitude in conjunction with the second determined amplitude to define the variable sensing threshold.

21. The apparatus of claim 20 wherein the means for defining a variable sensing threshold comprises means for defining a linearly decreasing sensing threshold.

22. The apparatus of claim 18 wherein the means for defining a variable sensing threshold comprises means for defining a linearly decreasing sensing threshold.

* * * * *

UNITED STATES PATENT AND TRADEMARK OFFICE
CERTIFICATE OF CORRECTION

PATENT NO. : 6,477,422 B1
APPLICATION NO. : 09/532574
DATED : November 5, 2002
INVENTOR(S) : Vincent E. Splett It is certified that error appears in the above-identified patent and that said Letters Patent is hereby corrected as shown below:

Title page,
Item [57], ABSTRACT, delete in its entirety and insert:
-- ABSTRACT
A method and apparatus for testing and detecting capture of the heart in response to a pacing pulse energy. The method includes deriving and storing stimulation threshold data and adjusting pacing pulse energy for energy efficiency. In one aspect of the invention, a pacing pulse is delivered via an electrode and the electrical signal is sensed using the electrode. Further, the amplitude of the sensed electrical signal is monitored over time. A polarization related amplitude of the sensed electrical signal is also determined from a second amplitude of the sensed electrical signal. The polarization related amplitude that is determined using the foregoing process is implemented to define a variable sensing threshold that decreases with time. Subsequently, the delivered pacing pulse responsive to the amplitude exceeding the variable sensing threshold for a defined duration is used to detect capture. --.

Signed and Sealed this

Twenty-fifth Day of July, 2006

JON W. DUDAS
*Director of the United States Patent and Trademark Office*